United States Patent [19]

Longmore et al.

[11] Patent Number: 4,822,338

[45] Date of Patent: Apr. 18, 1989

[54] METHOD OF REMOVING MATERIAL FROM THE STOMACH USING A COLLAPSIBLE FUNNEL

[76] Inventors: Wayne D. Longmore, 40 Remsen St., Apt. 4, Brooklyn, N.Y. 11201; Peter J. Acker, 49 Barton Pl., Port Chester, N.Y. 10573

[21] Appl. No.: 92,741

[22] Filed: Sep. 3, 1987

[51] Int. Cl.⁴ .............................................. A61M 31/00
[52] U.S. Cl. ......................................... 604/54; 604/96
[58] Field of Search ..................... 604/28, 54, 96, 104, 604/105, 256, 270; 128/DIG. 25

[56] References Cited

FOREIGN PATENT DOCUMENTS 1092161 11/1960 Fed. Rep. of Germany ........ 604/96
2847633 5/1979 Fed. Rep. of Germany ........ 604/96
2818119 11/1979 Fed. Rep. of Germany ........ 604/96

*Primary Examiner*—John D. Yasko
*Attorney, Agent, or Firm*—Darby & Darby

[57] ABSTRACT

A method of removing material from the stomach of a patient in which a collapsible funnel at the end of a catheter is placed into the stomach, the funnel is erected, lavage solution is applied through the catheter to the stomach and the patient is inverted to discharge the material from the stomach into the funnel's open end. In a preferred embodiment, the funnel is erected by inflation.

6 Claims, 1 Drawing Sheet

METHOD OF REMOVING MATERIAL FROM THE STOMACH USING A COLLAPSIBLE FUNNEL

BACKGROUND OF THE INVENTION

Various situations arise wherein a person ingests too many capsules of a vitamin or medicinal substance. The capsules must be removed before they dissolve and are distributed into the bloodstream and other parts of the human body where they could cause harmful effects.

One example of this is the ingestion of ferrous sulfite tablets. The inability to remove such tablets by conventional methods, such as vomiting and gastric labage using large orgastic tubes, with the consequent adverse effect has been documented clinically. One conventional way of removing the tablets of the type under consideration is by the use of a 40 French Lavacuator. Even the best results in using this approach have accounted for less than 50% of the removal of the tablets. Similarly, low yields of removal have resulted with the use of an E-Wald red rubber tube. Tablets containing ferrous sulfate (iron) are radio-opaque and failure of removal is easily identifiable. Ferrous sulfate tablets have been removed surgically when conventional techniques have not resulted in the removal of toxic amount of iron from the stomach. Of course, surgery is desirably avoided if at all possible.

BRIEF DESCRIPTION OF THE PRESENT INVENTION

The present invention provides a novel method and apparatus for increasing the removal rate of capsules from the stomach. In accordance with the invention, there is a funnel which is collapsible and attached to the end of a catheter. The funnel is inserted through the mouth of the patient and his esophagus into the appropriate place in his stomach. The collapsible funnel is then expanded into true funnel shape. The lavage solution is then applied through the funnel into the patient while in a substantially horizontal position. The orientation of the patient is then changed to one in which his head is down, for example, to about 75 degrees with respect to the horizontal. The capsules flow by gravity from the stomach into the funnel and through the catheter for exit from the patient's body.

With the use of such method and apparatus, it has been demonstrated in laboratory conditions that removal rates of approximately 70% of the capsules can be achieved.

OBJECTS OF THE INVENTION

It is therefore an object of the present invention to provide a novel method and apparatus for removing capsules from the stomach of a patient.

A further object is to provide a novel apparatus for use and removal of the capsules from the stomach of a patient which includes a catheter having a collapsible funnel which is expanded into its normal shape while in the stomach.

An additional object is to provide a novel method and apparatus wherein a funnel attached to the end of a catheter is inserted into the stomach of a patient, the patient is oriented to a position wherein the capsules can flow by gravity into the funnel and out of the body of the patient.

BRIEF DESCRIPTION OF THE DRAWINGS

Other objects and advantages of the present invention will become more apparent upon reference to the following specification and annexed drawings in which.

DETAILED DESCRIPTION OF THE INVENTION

Figure 1:
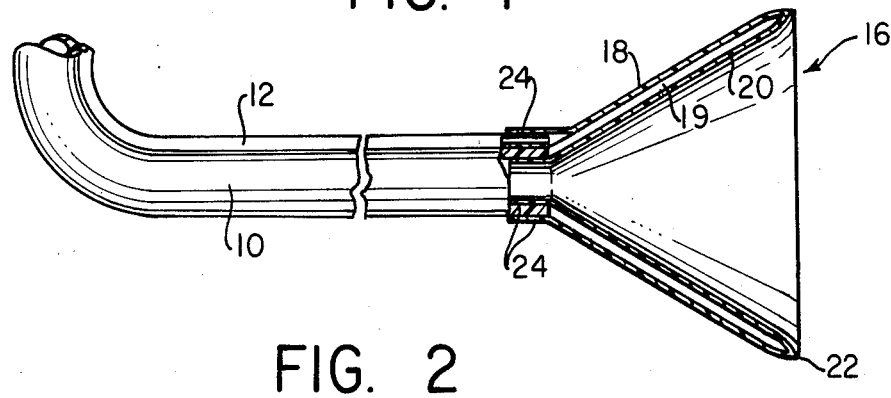
FIG. 1 is a perspective view of the apparatus in accordance with the invention.
Figure 2:
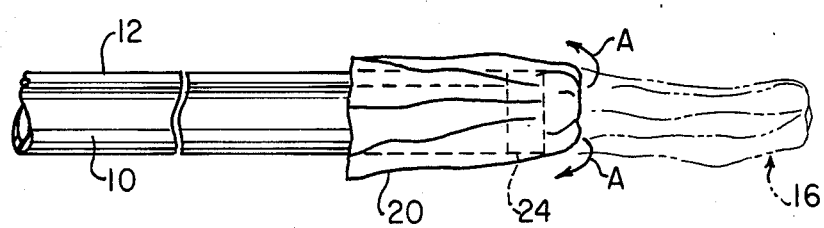
FIG. 2 is a perspective detailed view of the funnel in a collapsed condition.

Referring to FIGS. 1 and 2, there is shown a preferred embodiment of the apparatus of the present invention. This includes a hollow, flexible catheter 10 of a suitable sterilizable material. The catheter outer maximum diameter in such so it can be inserted into a patient's stomach through his mouth and an inner diameter such as to be able to evacuate the capsules. The catheter 10 can have any desired length.

There is attached to the catheter 10 along the substantial portion of its length a funnel inflation tube 12. The attachment can be, for example, by any suitable heat sealing, adhesive, etc. The diameter of the funnel inflation tube 12 is not critical since, as described below, only a small amount of fluid must be inserted through the tube 12 to achieve its function.

At the end of the catheter 10 there is a funnel 16 of the flexible material which is of the collapsible type. As shown in its example form in FIG. 1, the funnel is in the usual trumcated conical shape, although any other shape can be used. The funnel 16 is formed of any suitable material, for example two sheets 18, 20 of polyethylene of any other suitable material of appropriate thickness which can be rolled, folded, twisted, etc. The two sheets have space 19 therebetween into which a fluid can flow to erect and collapse the funnel.

The sheets 18 and 20 are sealed, such as by heat sealing or an adhesive at the end edges 22 of the maximum diameter of the funnel with a fluid tight seal. At the narrow end of the funnel, the two sheets 18 and 20 are sealed in a fluid tight manner around the outside of the catheter 10, as shown by the sealing areas 24, except in the location where the fluid insertion tube 12 meets the funnel. Here, the inner layer 20 of the funnel is sealed to the catheter 10 and the outer layer 18 is sealed around the fluid insertion tube 12. All of the seals mentioned are fluid tight seals. In this manner, there is communication with the space 19 between the two sheets 18 and 20 forming the funnel.

When enough fluid is supplied through the tube 12 to the space 19, the funnel will be erected to its desired shape. The fluid inserted through the insertion tube 12 to the funnel can either be air or a liquid. A liquid is preferred since if there is leakage in any of the sealing areas 22 or 24 around the upper and lower edges of the funnel, that there will still be enough liquid in the space 19 to substantially preserve the funnel in its intended erected shape. Also, as should be understood, the shape of the funnel will be irregular and collapsible in an area where it encounters a part of the body. That is, the funnel is erect, but it is "soft", i.e., its shape is pliable and conformable. Use of air as the inflation fluid also will accomplish the same result.

FIG. 2 shows the funnel 18 in its collapsed form. Since the sheets 18 and 20 which form the funnel are thin, they can be distorted, and twisted in any manner desired consistent with the physical properties of the sheets. For example, they can be folded back along the length of the catheter 10 by 180, from the direction shown in FIG. 2. In this arrangement, upon inflation, the funnel will not only be expanded into its truncated generally conical shape but also would be pushed forward off of the catheter 10. Such an arrangement is preferred since, for example, it permits insertion of the funnel and catheter 10 more easily through the esophagus into the stomach of a patient since the total package of funnel and catheter would have a minimum diameter. Alternatively, depending upon the size and shape of the funnel, it can be stuffed within the inner diameter of the catheter 10. In this case, upon inflation, the funnel would be pushed out of the catheter.

To supply the fluid to the funnel insertion tube 12, any suitable arrangement can be utilized. For example, there can be a syringe which is manually operated with air or water as the fluid source. There also can be an automatic fluid insertion device, e.g. a pump, which will maintain a constant fluid pressure. Such devices are well known in the art.

It should be understood that the fluid which fills the inflated space 19 of the funnel also can be withdrawn to collapse the funnel so that it can be withdrawn from the patent.

Other funnel-inflation liquid tube arrangements can be utilized. For example, the funnel inflation space 19 can have a number of communicating inflation chambers and internal self-acting check valves which permit the chambers to be filled and therafter sealed to make a structure with greater integrity. Alternatively, a separate inflation fluid supply tube can be used for each chamber.

FIG. 3 shows in a broad schematic form the method in which the present invention is utilized.

Figure 3A:
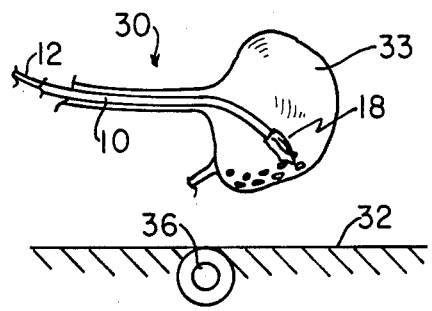
FIGS. 3A-3D, show the method of treatment using the invention.

As shown in FIG. 3A, the patient 30 is lying down on a table 32. The patient's stomach 33 is shown containing the tablets. The table 32 is of the tiltable type which can be rotated by a suitable mechanism 36 with appropriate locks from the horizontal position shown in FIG. 3A to, for example, a substantially vertical position in which the patient's head would be pointing directly down to the floor. Such table mechanisms are known in the art and form no part of the present invention.

As the first step in the procedure, the airway of the patient is cleared and protected.

As shown in FIG. 3A, the catheter 10 with the attached fluid insertion tube 12 along its length and the funnel 18 at one end is inserted into the patient's stomach through his esophagus.

For insertion into the patient's stomach, the catheter and funnel can be contained within an outer catheter. The outer catheter is inserted into the desired location and is then removed leaving the catheter 10 and the funnel 1 in the proper place for inflation of the funnel. Such arrangements are used, for example, in the intra-aortic balloon art. If desired, either the funnel 18 or part of the catheter 10 can be supplied with the radioactive marker so that the process can be viewed by x-rays as it has been carried out.

The funnel is positioned near the desired location. It is preferred, for example, that when the funnel is open, the wider diameter top end will be positioned approximately as shown in FIG. 3D.

Figure 3B:
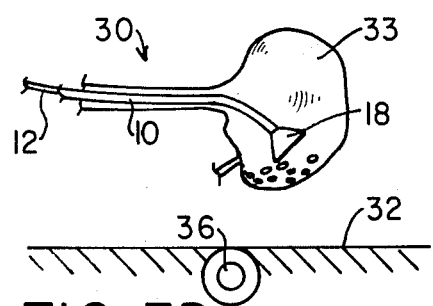

The funnel is then inflated, as shown in FIG. 3B with the patient still in a horiztonal position. The inflation is carried out, as indicated before, either manually by a syringe or using an automatic device to pass fluid through the inflation tube 12 to the funnel.

Figure 3C:
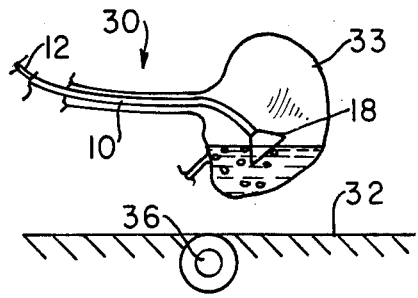

With the patient still in the horizontal position as shown in FIG. 3C and with the funnel 18 inflated, a lavage solution is passed into the patient's stomach. A typical amount of a lavage solution would be one liter of a saline solution. The lavage solution dislodges the tablets from the mucous of the stomach lining where they may have become lodged and causes the pills to float or at least be movable within the total fluid contents of the stomach.

Figure 3D:
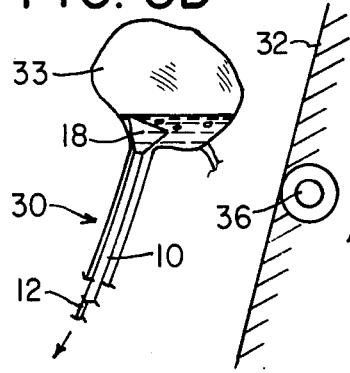

As shown in FIG. 3D, the patient is then turned to a substantially vertical position, for example, 75, from the horizontal, by the use of the table rotating and locking mechanism 36. The pills flow into the expanded funnel 18 by gravity and out through the catheter 10. In this manner, the tablets are removed from the patient's stomach. If desired, an amount of suction can be applied to the catheter to aid in the removal of the tablets. That is, the suction will draw the material into the funnel and through the catheter.

Since the funnel is available, there is a substantially increased probability of removing the tablets. There is a wide entry area into the funnel, which entry area leads to the catheter 10 through which the pills are extracted. This wide entry area is not available in presently available devices.

The process outlined above, with respect to FIG. 3C, the lavage and FIG. 3D, moving the patient to a more vertical position, can be carried out several times, for example, up to 10 times, to increase the percentage of tablets which will be extracted.

AFtger the process is completed, the funnel is deflated by withdrawing the inflation fluid from the space 19. The catheter with the attached funnel is then withdrawn from the patient.

Experiments utilizing the present invention have been carried out with dogs. Two test regimens were followed. These are explained below.

In the first test, fifty tablets of 325 mg ferrous sulfate were placed in the stomach of a dog. The following results were obtained.
  a. after 50 trials with the funnel lavage apparatus and gravity withdrawal technique of the present invention, there was an average of 87.4% of the tablets removed with five liters of lavage. An average of 43.7 pills out of the fifty placed in the stomach were removed.
  b. After 20 trials with the 40 French Lavacuator less than 5% of the fifty pills placed in the stomach were removed after 5 liters of lavage. That is, an average of 2.5 pills of the 50 placed in the stomach were removed.
  c. After 25 trials with the red rubber E-Wald tube, less than 5% of the 50 pills placed in the stomach on average were removed. That is, an average of 2.5 of the 50 tablets placed in the stomach were recovered.

In the second test, 50 tablets of 325 mg ferrous sulfate were placed in the stomach of dogs and left for 2 hours before evacuation was attempted. The results were as follows:
  a. Five trials with the funnel lavage apparatus and gravity technique of the present invention yielded a retrieval of an average of 70% of the 50 tablets with 5 liters of lavage. Therefore, average of the 35 of the 50 tablets placed were removed.

b. After five trials with the 40 French Lavacuator an average of less than 5% of the 50 tablets were removed after 5 liters of lavage. That is, an average of about 2.5 of the 50 tablets were removed.

c. After five trials with the red rubber E-Wald tube less than 5% of the 50 tablets were removed. An average of less than 2.5 of the 50 tablets were removed.

Internal examination of the dogs found that in 80% of the two hour delayed trials, the stomach was found to be hyperemic with evidence of ulceration of the mucousa. In general, the pills were intact and had formed loose association with other pills by means of mucous in the stomach sticking the tablets together. Many of the tablets not removed appeared to be adherent to the stomach mucousa.

We claim:

1. A method of removing material from the stomach of a patient comprising the steps of:

inserting a catheter with a collapsible funnel into the stomach of a patient, erecting the funnel, administrating a lavage liquid through the catheter to the patient's stomach, and turning the patient to a position where his head is lower than his feet to permit the material to be removed to flow from the stomach into the open end of the funnel and out of the patient through the catheter.

2. A method as in claim 1 wherein the funnel is inflatable and the catheter is inserted into the patient with the funnel collapsed and the funnel is thereafter inflated while in the stomach into the erected shape.

3. A method as in claim 1 wherein the lavage solution is administered with the patient in a generally horizontal position.

4. A method as in claim 3 herein the steps of administering the lavage solution and turning the patient to a head down position is carried out repetitively.

5. A method as in claim 1 wherein the inserting step comprises providing a funnel of generally conical shape and the funnel is inserted into the patient so that the material to be removed flows into the wide end of the funnel.

6. A method as in claim 1 wherein the step of inserting the catheter with funnel comprises the step of providing an inflatable funnel of generally conical shape, and the step of erecting the funnel comprises inserting the catheter into the patient with the funnel collapsed and thereafter inflating the funnel while in the stomach.

* * * * *